(12) United States Patent
Massengale

(10) Patent No.: US 8,052,651 B2
(45) Date of Patent: Nov. 8, 2011

(54) APPARATUS AND METHOD FOR SECURING A CATHETER WITHIN AN ANATOMY

(75) Inventor: Roger Massengale, Mission Viejo, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/113,858

(22) Filed: May 1, 2008

(65) Prior Publication Data
US 2008/0300548 A1 Dec. 4, 2008

Related U.S. Application Data

(60) Provisional application No. 60/915,753, filed on May 3, 2007.

(51) Int. Cl.
*A61M 5/32* (2006.01)
(52) U.S. Cl. ........................................................ 604/175
(58) Field of Classification Search .................. 604/174, 604/175, 176, 177, 178, 179, 180
See application file for complete search history.

(56) References Cited

U.S. PATENT DOCUMENTS

| | | | |
|---|---|---|---|
| 4,311,148 A | 1/1982 | Courtney et al. | |
| 5,318,527 A | 6/1994 | Hyde | |
| 5,458,570 A | 10/1995 | May | |
| 5,527,293 A | 6/1996 | Zamierowski | |
| 5,735,829 A | 4/1998 | Cherian | |
| 5,782,747 A | 7/1998 | Zimmon | |
| 5,954,694 A | 9/1999 | Sunseri | |
| 6,042,577 A | 3/2000 | Chu et al. | |
| 6,258,061 B1 | 7/2001 | Drasler et al. | |
| 6,302,875 B1 | 10/2001 | Makower et al. | |
| 6,315,789 B1 | 11/2001 | Cragg | |
| 6,482,184 B1 | 11/2002 | Christensen et al. | |
| 6,554,802 B1* | 4/2003 | Pearson et al. | 604/177 |
| 6,562,005 B1 | 5/2003 | Donath | |
| 2002/0007130 A1 | 1/2002 | Burbank et al. | |
| 2004/0073194 A1 | 4/2004 | Olsen et al. | |
| 2004/0225297 A1 | 11/2004 | Chen | |
| 2005/0277862 A1* | 12/2005 | Anand | 604/4.01 |
| 2006/0206096 A1 | 9/2006 | Accisano et al. | |

FOREIGN PATENT DOCUMENTS

| | | |
|---|---|---|
| EP | 1 025 802 | 8/2000 |
| WO | WO 02/26309 | 4/2002 |
| WO | WO 2004/101052 | 11/2004 |

OTHER PUBLICATIONS

International Search Report for Application No. PCT/US2008/062282, mailed Jul. 31, 2008 (PCT/US2008/062282 is the corresponding PCT application of the present application).

* cited by examiner

*Primary Examiner* — Kevin C Sirmons
*Assistant Examiner* — Brandy C Scott
(74) *Attorney, Agent, or Firm* — Dority & Manning, P.A.

(57) ABSTRACT

An apparatus and method for securing a catheter within a target area of the anatomy are disclosed. The catheter includes a passage or opening through which a suture filament may be routed. The suture filament can be secured relative to anatomical tissue to retain the catheter within a desired region. After the catheter has been used to complete the desired medical procedure, the suture filament may be released, permitting the catheter to be easily withdrawn from the anatomy. The catheter may include a biodegradable tip, which when absorbed by the body would enable the catheter to be removed. Biodegradable suture filaments and other components may also be used to facilitate the release of the catheter from the anatomy.

8 Claims, 8 Drawing Sheets

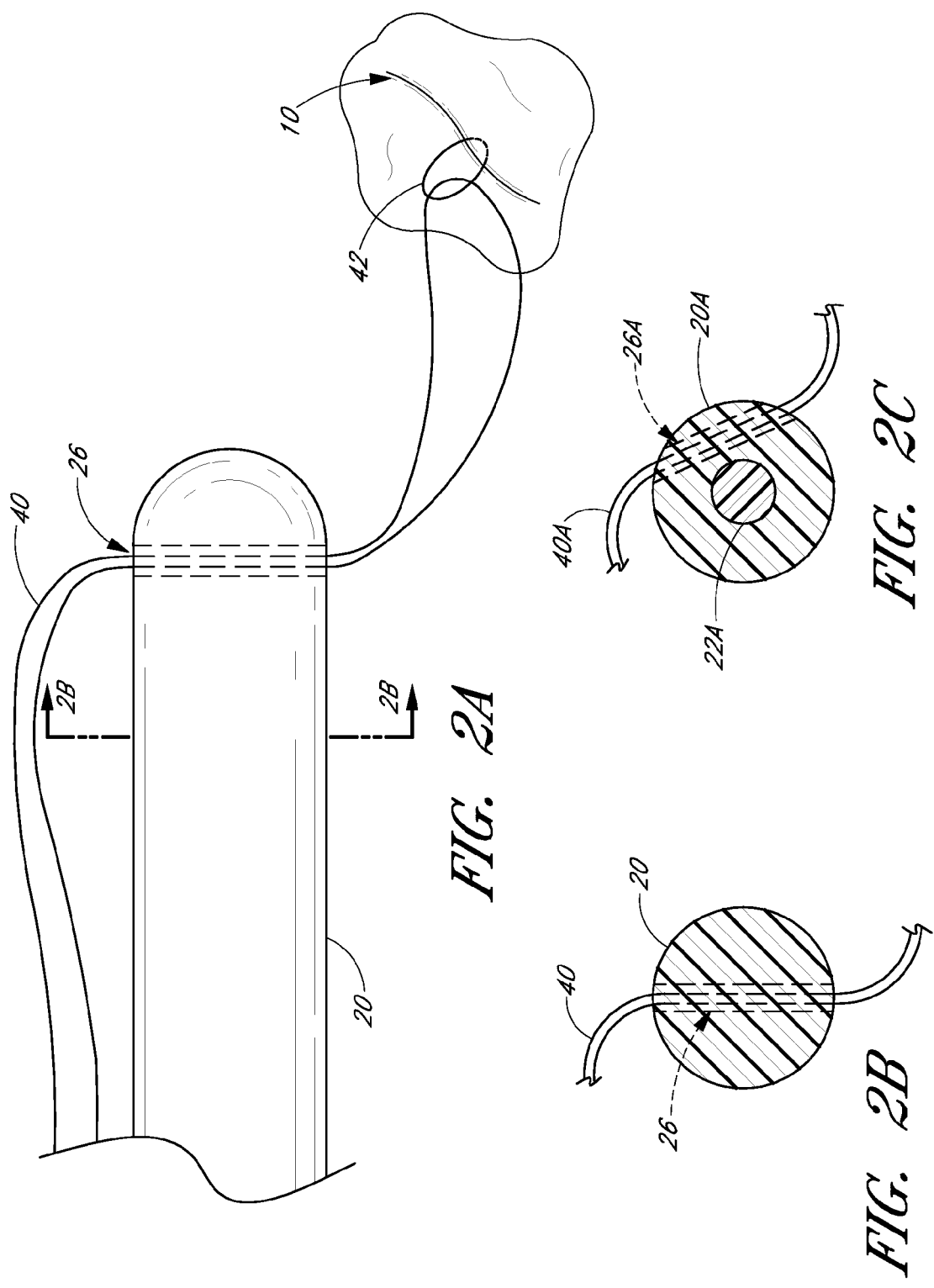

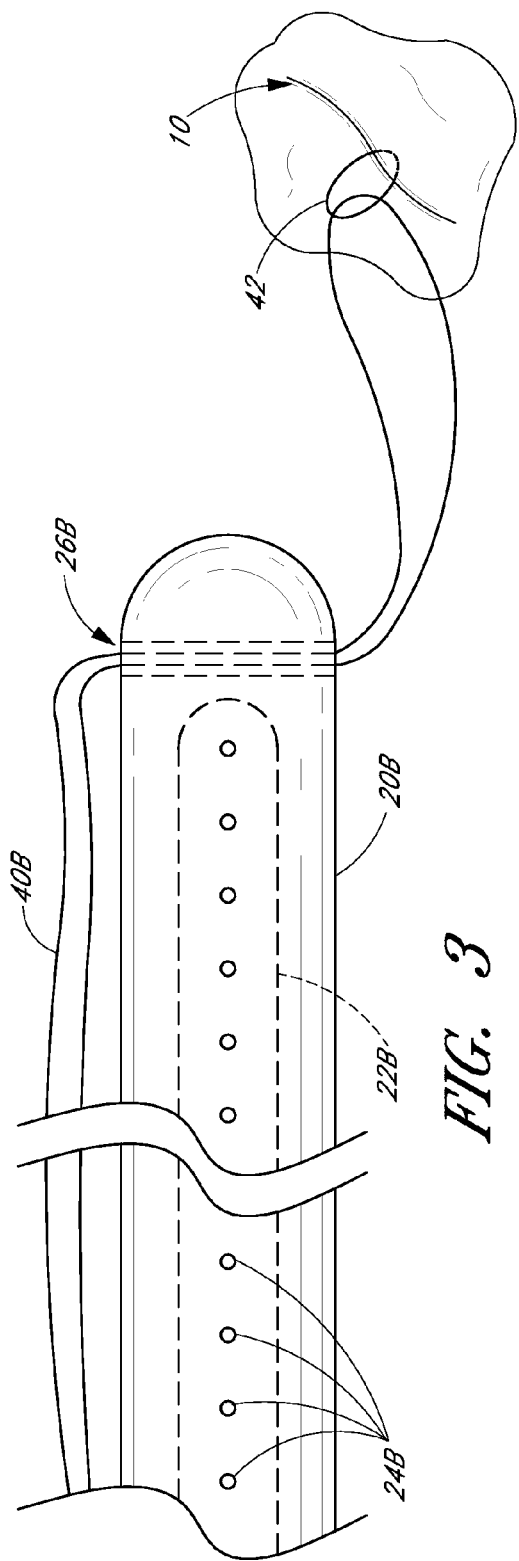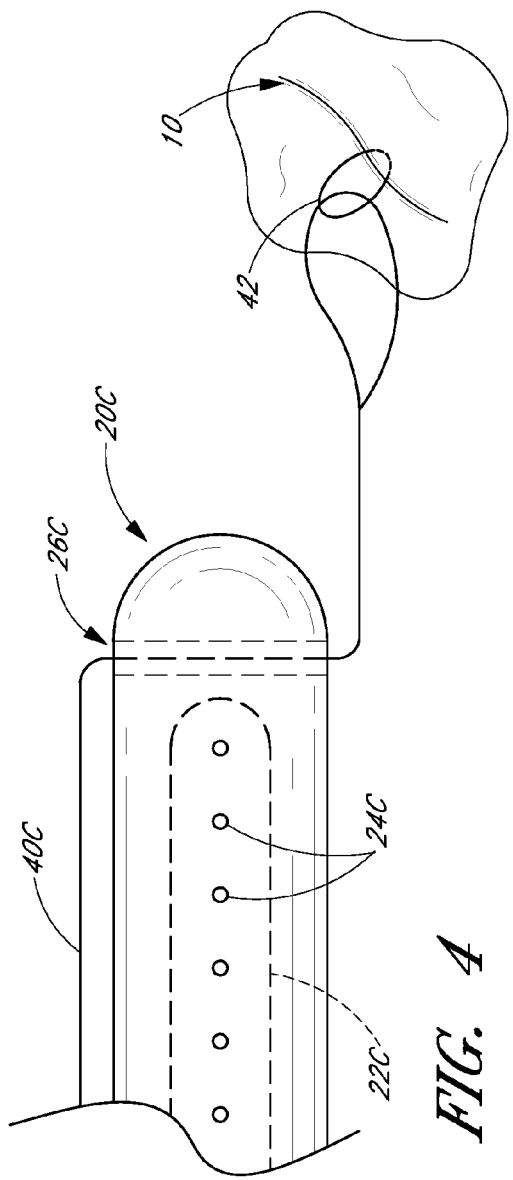

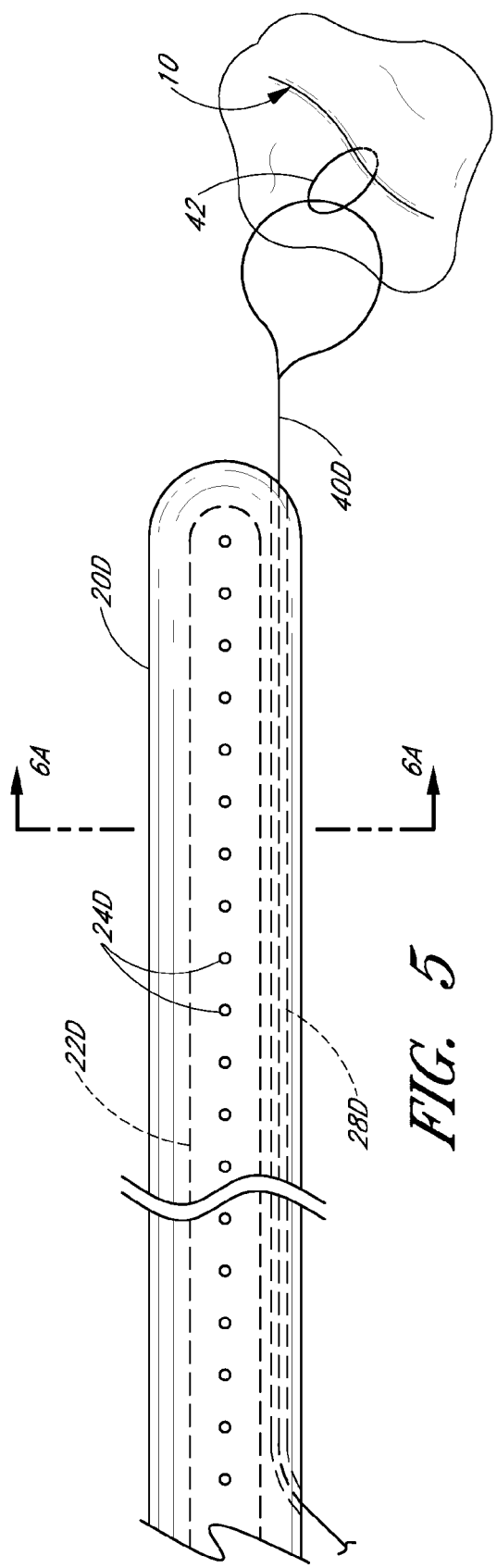
FIG. 5
FIG. 6A
FIG. 6B

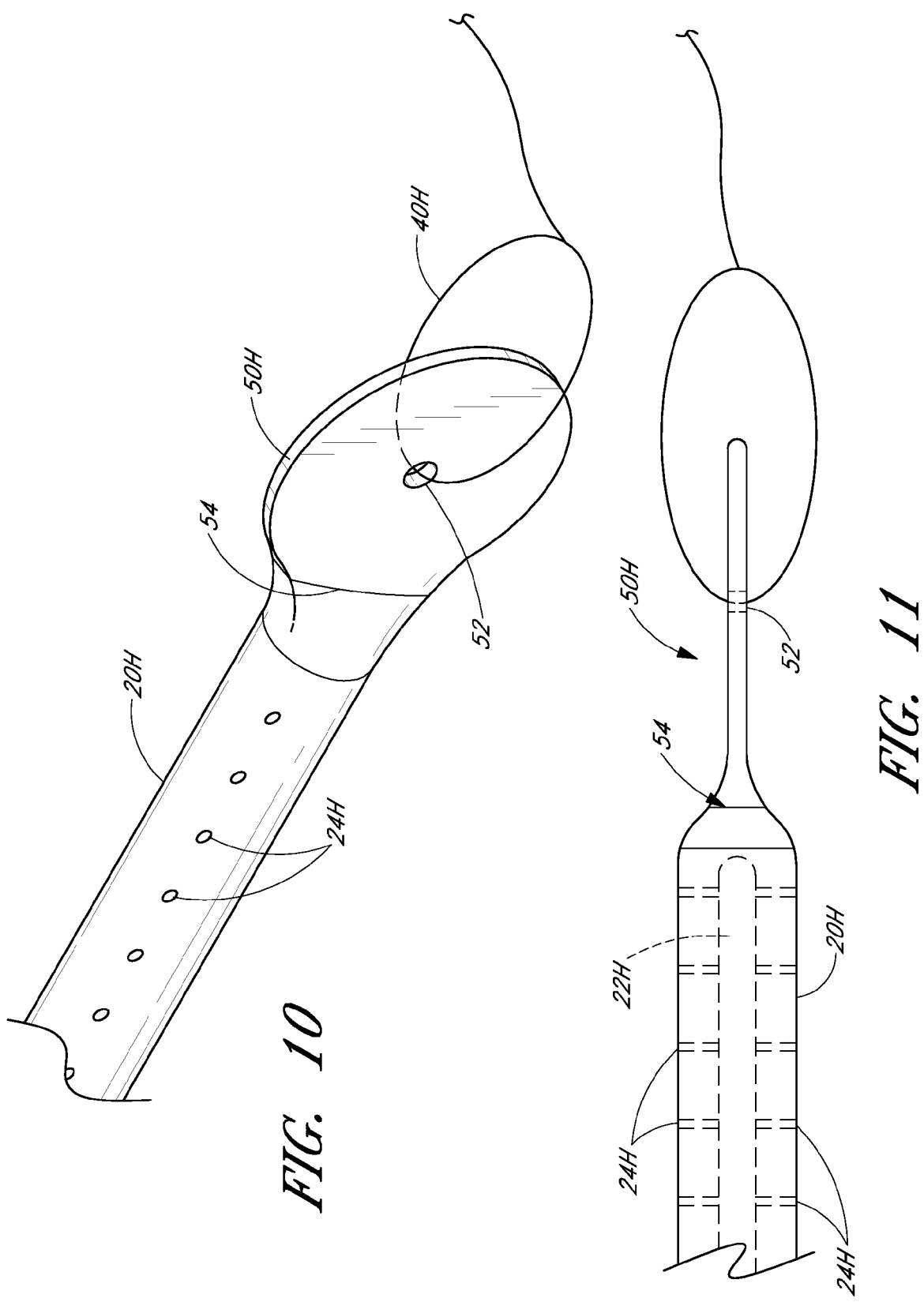

APPARATUS AND METHOD FOR SECURING A CATHETER WITHIN AN ANATOMY

CROSS-REFERENCE TO RELATED APPLICATIONS

This application claims the priority benefit under 35 U.S.C. §119(e) of U.S. Provisional Application No. 60/915,753, filed May 3, 2007, the entirety of which is hereby incorporated by reference herein.

BACKGROUND OF THE INVENTION

1. Field of the Invention

This application relates generally to devices configured for placement within an anatomy and methods of using same, and in particular, to attachable and detachable catheter devices and methods of using same.

2. Description of the Related Art

Catheters, tubes and other medical devices are introduced into the anatomy during different types of medical procedures. Once delivered, such devices provide direct access to a targeted organ, cavity or other site within the anatomy for a variety of therapeutic, diagnostic and other medically-related purposes. Often, it is desirable to secure the catheter or similar device within a desired site of the anatomy in order inhibit undesired movement or retraction of the catheter. Typically, after the procedure or activity is completed, the catheter or other device is withdrawn from the anatomy. However, with existing devices and methods, removal of the catheter is difficult, and may cause discomfort to the patient.

SUMMARY OF THE INVENTION

An aspect of the present invention involves a catheter for placement in an anatomical region, comprising an elongated catheter body defining a longitudinal axis and having a proximal end portion and a distal end portion. The catheter body defines a lumen extending along the longitudinal axis. A passage is located within the distal end portion of the catheter body and extends across the catheter body such that the passage has a directional component generally perpendicular to the longitudinal axis. The passage is isolated from the lumen and is configured to accept a filament for securing the catheter device to a portion of the anatomical region.

Another aspect of the present invention involves a catheter for placement in an anatomical region that includes an elongated catheter body defining a longitudinal axis. The catheter body has a proximal end portion and a distal end portion. A first lumen extends along the longitudinal axis and is configured to deliver fluid between the proximal and distal end portions. A second lumen is isolated from the first lumen and is situated within a portion of the catheter body. The second lumen has a distal opening located near the distal end portion of the catheter body and a proximal opening spaced proximally along the longitudinal axis from the distal opening. The second lumen is configured to accept a filament for securing the catheter device to a portion of the anatomy. The portion of the catheter body containing the second lumen has a substantially circular cross-sectional shape.

Still another aspect of the present invention involves a catheter for placement in an anatomical region that includes an elongated body having a proximal end portion and a distal end portion. A tip member is releasably secured to the distal end portion of the elongated body. The tip member includes a passage configured to accept a filament for securing the catheter within the anatomical region.

Yet another aspect of the present invention involves a method of removing a catheter from an anatomical region. The method includes applying a force to a filament that secures the catheter within the anatomical region to cause the filament to pass from a lumen of the catheter, through a slit in the wall of the catheter, to outside of the catheter to permit removal of the catheter from the anatomical region.

Another aspect of the present invention involves a method of removing a catheter, which includes a catheter body and a biodegradable tip secured to the catheter body, from an anatomical region. The method includes waiting a sufficient period of time after the catheter has been placed within the anatomical region for the biodegradable tip, which is secured within the anatomical region, to degrade to a sufficient degree such that the catheter body can be separated from the biodegradable tip. The method further comprises applying a force to the catheter body to separate the catheter body from the biodegradable tip.

BRIEF DESCRIPTION OF THE DRAWINGS

These and other features, aspects and advantages of the present devices and methods are described in detail below with reference to drawings of certain preferred embodiments, which are intended to illustrate, but not to limit, the present inventions. The drawings contain fourteen (14) figures. It is to be understood that the attached drawings are for the purpose of illustrating concepts of the present inventions and may not be to scale.

FIG. 2A is a side view of the distal end portion of the catheter of FIG. 1 with the passage and a portion of the suture loop within the passage shown in broken line.

FIG. 2B is a cross-sectional view of the catheter of FIGS. 1 and 2A taken along view line 2B-2B of FIG. 2A.

FIG. 2C is a cross-sectional view of a modification of the catheter of FIG. 2B.

FIG. 3 is a side view of the distal end portion of the catheter according to another embodiment, with certain portions of the catheter shown in broken line.

FIG. 4 is a side view of the distal end portion of the catheter according to yet another embodiment, with certain portions of the catheter shown in broken line.

FIG. 5 is a side view of the distal end portion of the catheter according to still another embodiment, with a first lumen and a second lumen shown in broken line.

FIG. 6A is a cross-sectional view of the catheter of FIG. 5 taken along view line 6A-6A of FIG. 5.

FIG. 6B is a cross-sectional view of a modification of the catheter of FIG. 6A in which the catheter wall includes a slit extending from the second lumen to the exterior surface of the catheter.

FIG. 10 is a perspective view of a catheter having an enlarged tip portion at its distal end according to one embodiment.

FIG. 11 is a side view of the catheter of FIG. 10 with certain portions of the catheter shown in broken line.

DETAILED DESCRIPTION OF THE PREFERRED EMBODIMENTS

Catheters are used in a variety of medical applications. For example, catheters are often used to facilitate the administration of intravenous liquids, medications or other fluids within the anatomy. In addition, catheters may be used for draining unwanted fluids from an organ, cavity or other part of the anatomy. Further, catheters may be used as passageways for other instruments and medical devices. Consequently, it may be desirable to secure a catheter within the anatomy to prevent the catheter from migrating away from a target site. For example, a catheter may be left within the anatomy for an extended time period, during which the patient is permitted to freely move. In such situations, the patient's bodily motions, the natural movements of the catheter itself within the anatomy and/or other forces acting upon the catheter can cause the catheter to move away from the site targeted for treatment. This may lead to ineffective treatment, discomfort or even injury to the patient. Desirably, a catheter can be configured to be easily released from the anatomy for the subsequent removal of the catheter.

Figure 1:
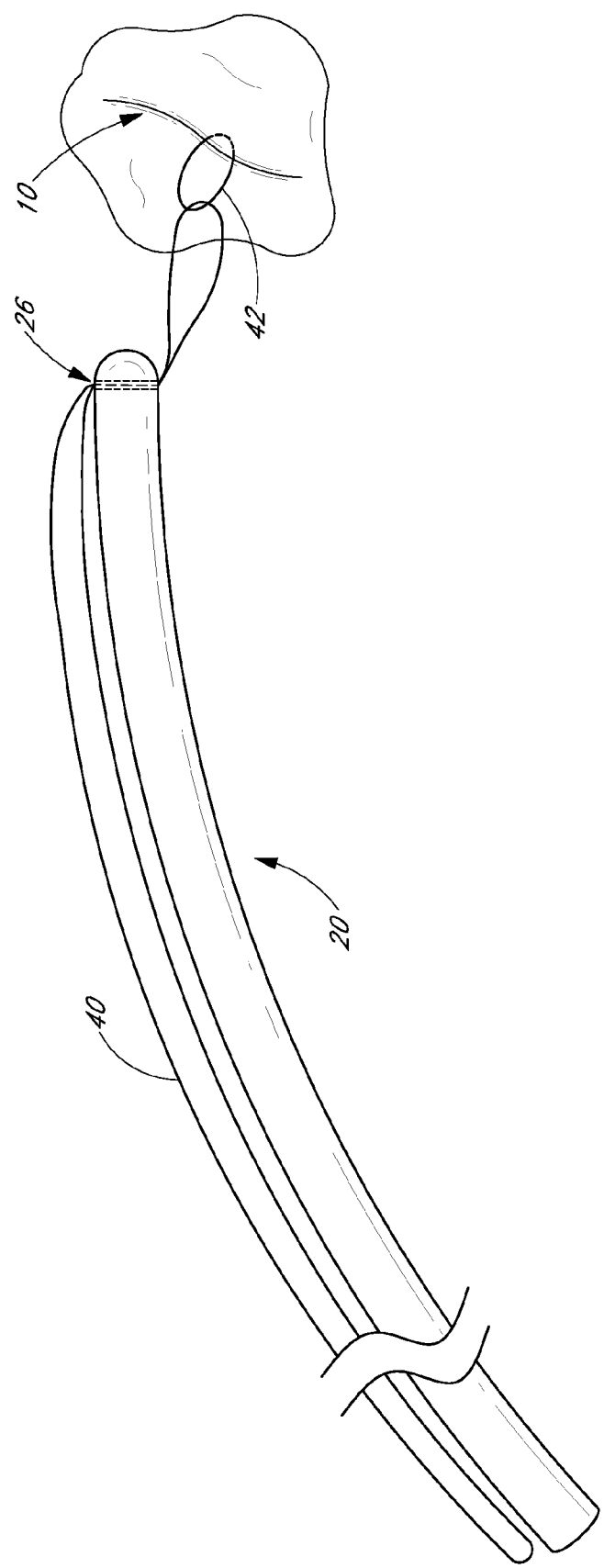
FIG. 1 is a perspective view of a catheter with a passage near its distal end configured to accept a suture loop for securing the catheter within an anatomy.

FIG. 1 illustrates a catheter 20 according to one or more embodiments of the present invention. As shown, the catheter 20 can include a passage 26, opening or other passageway through which a suture filament 40 or the like may be passed. In the depicted embodiment, a single passage 26 is situated near the distal portion of the catheter 20. However, those of skill in the art will appreciate that the passage 26 may be situated at any suitable location along the catheter. Further, the catheter 20 may include one or more additional passages along its elongated body. As illustrated, the entire suture filament 40 can be substantially formed into a loop that is secured to a secondary suture loop 42, which is connected, either directly or indirectly, to anatomical tissue 10. However, in other embodiments, the suture filament 40 may be directly attached to anatomical tissue 10. Moreover, the suture filament 40 may be formed into other shapes and configurations. Regardless of the exact attachment arrangement used, the passage of the suture filament 40 through the passage 26 and its attachment to anatomical tissue 10 advantageously restricts the movement of the catheter 20 within the anatomy.

Suture filament 40 may be manufactured from a variety of bioabsorbable and/or non-bioabsorbable materials, including, but not limited to, catgut, nylon, polypropylene, polyethylene, linen, cotton, silk, stainless steel wire, etc. Further, the suture filament 40 may include a single strand or a multiple (e.g., braided or twisted) strand design.

As illustrated in FIG. 2B, the transverse passage 26 at the distal end of the catheter 20 can have a generally cylindrical shape and can be configured to pass generally through the center portion of the catheter's cross section. In some embodiments, the transverse passage 26 intersects the longitudinal axis of the catheter 20. Preferably, the passage 26 is generally transverse to a longitudinal axis of the catheter; however, the passage 26 may be offset from the transverse direction, if desired. Thus, as used herein, "transverse" is intended to cover passages 26 that lie in a plane perpendicular to the longitudinal axis of the catheter 20 as well as passages that are slightly or substantially skewed from such a plane. Furthermore, the passage 26 may have a different orientation across the catheter body than that shown in FIG. 2B. For example, in the embodiment illustrated in FIG. 2C, the passage 26A extends through the cross section of the catheter 20A at a location spaced from the longitudinal axis of the catheter 20. Such an arrangement may be preferred to avoid interference with an inner lumen 22A and/or other feature of the catheter, especially when the passage 26A is positioned on the catheter 20 at a longitudinal position in which the lumen 22A is also present. It will be appreciated that the passage may have any suitable cross-sectional size and shape.

As illustrated in FIG. 3, the catheter 20B may include an inner infusion lumen 22B and a plurality of openings 24B in fluid communication with the infusion lumen 22B. Such catheters 20B are well-suited for channeling fluids (e.g., medications, anesthetics, excess bodily fluids, etc.) to and/or from sites within the anatomy. In the depicted embodiment, a passage 26B for receiving a suture loop 40B is provided immediately past the distal end of the lumen 22B. Thus, the passage 26B may be routed along the center cross-sectional portion of the catheter 20B without interfering with the lumen 22B. Alternatively, as discussed with reference to FIG. 2C above, the passage may extend through the catheter body along the longitudinal portion of the lumen without interfering with it, by passing through the catheter body along a path offset from the longitudinal axis of the catheter 20B. In other embodiments, the passage may be intentionally oriented through an infusion lumen of the catheter to provide additional infusion openings for the lumen.

FIG. 4 illustrates another embodiment of a suture filament 40C that is used to secure a catheter 20C within an anatomy. In the depicted arrangement, the suture filament 40C is formed into a loop only at its distal end for attachment to a secondary suture loop 42. Consequently, the portion of the suture filament 40C that passes through the passage 26C of the catheter 20C does not have a looped shape. As previously discussed, the suture filament 40C may be alternatively secured directly to anatomical tissue 10.

In the embodiments discussed herein, the suture filament is routed along the outside of the catheter body for substantially the entire length of the catheter (see, for example, FIG. 1). Alternatively, as illustrated in FIG. 5, the catheter 20D may include a filament lumen 28D, through which a suture filament 40D can be situated. In FIG. 5, the filament lumen 28D extends only through a distal portion of the catheter 20D. However, it will be appreciated that the filament lumen 28D may extend for the entire length of the catheter or over a greater portion of the catheter than depicted herein. However, in other arrangements, the filament lumen 28D is configured to extend over a shorter length of the catheter than illustrated herein. As shown in FIG. 6A, the filament lumen 28D may be advantageously positioned along the outside portion of the catheter's cross section so as to avoid interference with other catheter lumens 22D. Further, the filament lumen 28D may have any suitable cross-sectional shape and/or size.

Like in FIG. 6A, the filament lumen 28E shown in FIG. 6B is positioned along an outside portion of the catheter cross section, offset from the longitudinal axis of the catheter 20E. In the illustrated embodiment, the catheter 20E includes a slit 30 extending from the outer portion of the filament lumen 28E surface through the outside wall of the catheter 20E. As is described in greater detail below, upon the application of a minimum radial force on the suture filament 40E, the slit 30 can be configured to permit the suture filament 40E to pass from the filament lumen 28E to the exterior of catheter 20E through the slit 30. In one embodiment, the minimum force necessary to move the suture filament 40E through the slit 30 is approximately ¼ lb. However, it will be appreciated that in other arrangements, the minimum force may be greater or less than ¼ lb, as desired or required. For example, the minimum necessary force may be about ⅛ lb or less. Alternatively, the minimum necessary force may be about 2-5 lbs, or greater. In other arrangements, such a minimum force can range between ⅛ lb and 2 lbs.

Figure 7:
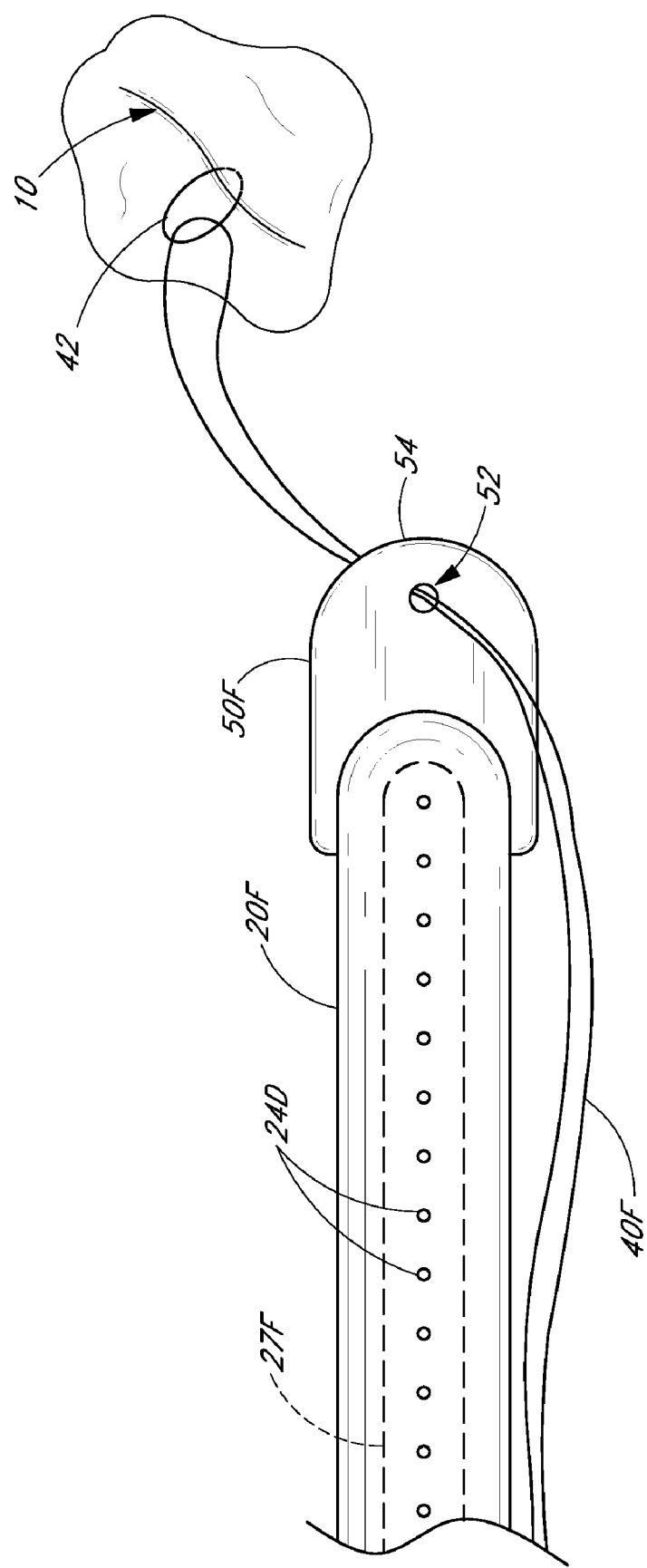
FIG. 7 is a view of a catheter having a tip member secured to its distal end according to one embodiment.

In FIG. 7, a tip 50F is attached to the distal end of the catheter 20F. The tip 50F preferably includes a passage 52 through which a suture filament 40F may pass. Similarly to the other embodiments discussed herein, the suture filament 40F can be secured to the anatomy 10, either directly or through a separate filament loop 42. The tip 50F can comprise silicone, stainless steel, plastic and/or other materials suitable for placement within the anatomy. Preferably, the tip 50F is manufactured from materials that make it more durable than the catheter 20F to which it is joined. This may permit the catheter 20F to be advanced to locations within the anatomy that otherwise might not be possible. The tip 50F may be joined to the catheter 40F using any of a variety of attachment methods or devices (e.g., glues, other adhesives, stitching, snug-fit connections and/or the like). Alternatively, the tip 50F and catheter 20F may be manufactured from a single or continuous structure or material. Thus, in some embodiments, the enhanced durability of the tip 50F may simply result from making the walls and/or other components of the tip 50F thicker. In other embodiments, the durability of the tip 50F is identical or less than that of the adjoining catheter 20F.

With continued reference to FIG. 7, the tip 50F may be generally wider than the distal portion of the catheter 20F which it surrounds. The tip 50F can have a generally cylindrical shape, allowing it to completely surround the entire distal end of the catheter 20F. Alternatively, the tip 50F may only encompass a portion of the catheter 20F. As depicted, the tip 50F has a rounded distal surface 54 that generally mimics the shape of the distal portion of the catheter 20F. However, the tip 50F can have any other size and/or shape, as desired or required. For instance, in FIG. 9, the depicted catheter 20G includes a cylindrically-shaped tip 50G that has a generally flat distal surface. In addition, the tip 50G illustrated in FIG. 9 encompasses a greater portion of the adjoining catheter 20G than the tip 50F of FIG. 7.

Figure 8:
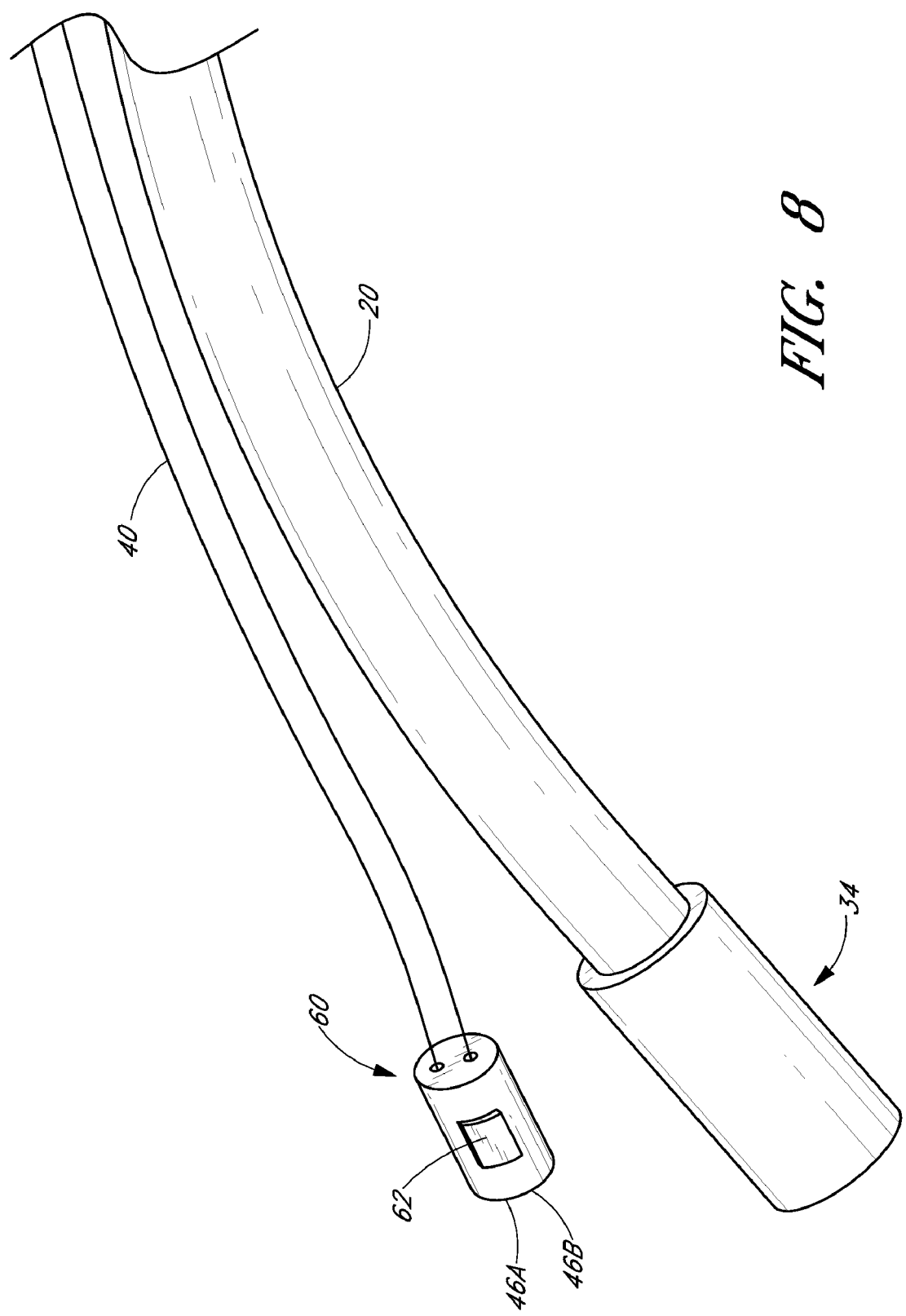
FIG. 8 is a perspective view of the proximal end of a catheter with a suture loop according to one embodiment.

FIG. 8 illustrates the proximal portion of a catheter 20 and suture filament 40 according to one embodiment. As shown, the proximal end of the catheter 20 can include a luer connector 34, catheter connector or other type of fitting. The two free ends 46A, 46B of the suture filament 40 can be secured within a locking device 60 to maintain the integrity of the suture loop. Alternatively, the free ends 46A, 46B of the suture filament 40 may be held together using any other suitable method or device, including, but not limited to, other types of gripping members (e.g., toggles, pliers type clamps, other type of clamps, etc.), tying or gluing the free ends 46A, 46B to one another and/or the like. In some embodiments, the locking device 60 or other gripping member is either attached to or in close proximity to the luer connector 34 or similar fitting. This can help provide to a user an easy method of releasing the suture filament 40 while the catheter 20 is being manipulated.

In the illustrated arrangement, the locking device 60 includes a button 62, which allows the suture filament 40 to be released when pressed. A suture loop may also be broken by simply cutting the suture filament 40 in at least one location. For example, the locking device 60 may be configured so that actuation of the button 62 cuts or otherwise compromises the suture filament 40. In other embodiments, the catheter may be configured so as to permit the suture filament 40 to be cut or otherwise weakened at more distal locations along the length of the suture filament 40. After the suture filament 40 is released, the catheter 20 can be easily withdrawn as it is no longer secured to anatomical tissue. It is to be understood that in the above embodiments involving the locking device 60, or similar release member, the suture filament 40 may include a single strand, a loop portion or any other configuration. In addition, the locking device 60 or similar release member may be configured to alter the tension within the suture filament 40. For example, a handle or other device may be provided to wrap the suture filament around a spindle. In other embodiments, the tension and/or slack in the suture filament 40 can be controlled by feeding the suture filament into and/or out of an eyelet and/or using any other suitable method.

Alternatively, biodegradable suture filament may be advantageously used to temporarily secure the catheter within an anatomical location. The biodegradable suture filament can be configured to breakdown after situated within the anatomy for a particular time period. Consequently, the need to cut or otherwise undermine the filament suture is eliminated. Thus, once the suture filament is absorbed, dissolved or otherwise compromised, the catheter could be easily withdrawn. In such arrangements, the entire suture filament is preferably manufactured from one or more biodegradable materials. Alternatively, only a portion of the suture filament may include a biodegradable material. Thus, it might be necessary to remove the remaining portion of the suture filament from the anatomy once the biodegradable section is absorbed by the body.

The biodegradable suture filament may be manufactured from or may comprise any suitable synthetic and/or natural materials. In a preferred embodiment, the type, size (e.g., diameter, thickness, gauge, etc.) and/or other material properties of the suture filament are selected according to the desired time period that an attached catheter will remain within the anatomy (e.g., 1 hour, 1 day, 3-10 days, 2 weeks, etc.). In addition, one or more other suture filaments used in securing the catheter to a target area within the body may also be manufactured from biodegradable materials (e.g., the secondary suture loops 42 as shown in FIGS. 1, 2A, 3-5, 7 and 9).

In other embodiments, a catheter may be configured to detach from the anatomy without the need to release a suture filament. For example, in FIG. 9, a biodegradable tip 50G is attached to the distal end of the catheter 20G. The illustrated tip 50G includes one or more passages 52 through which a suture filament 40G may be passed. The catheter 20G is maintained within the targeted site of the anatomy by securing the suture filament 40G to anatomical tissue, either directly or indirectly. The tip 50G can be connected to the catheter 20G using any suitable method. In some embodiments, a biodegradable adhesive is used to attach the tip 50G to the catheter 20G. Alternatively, the tip 50G may be stitched, glued and/or otherwise joined to the catheter 20G. In other embodiments, the tip 50G may be stitched to the catheter 20G using biodegradable and/or non-biodegradable sutures. In another arrangement, a simple snug-fit or friction-fit connection can be used to secure the tip 50G to the distal end of the catheter 20G, especially if the forces to which the catheter 20G will be subjected within the body are relatively low.

Figure 9:
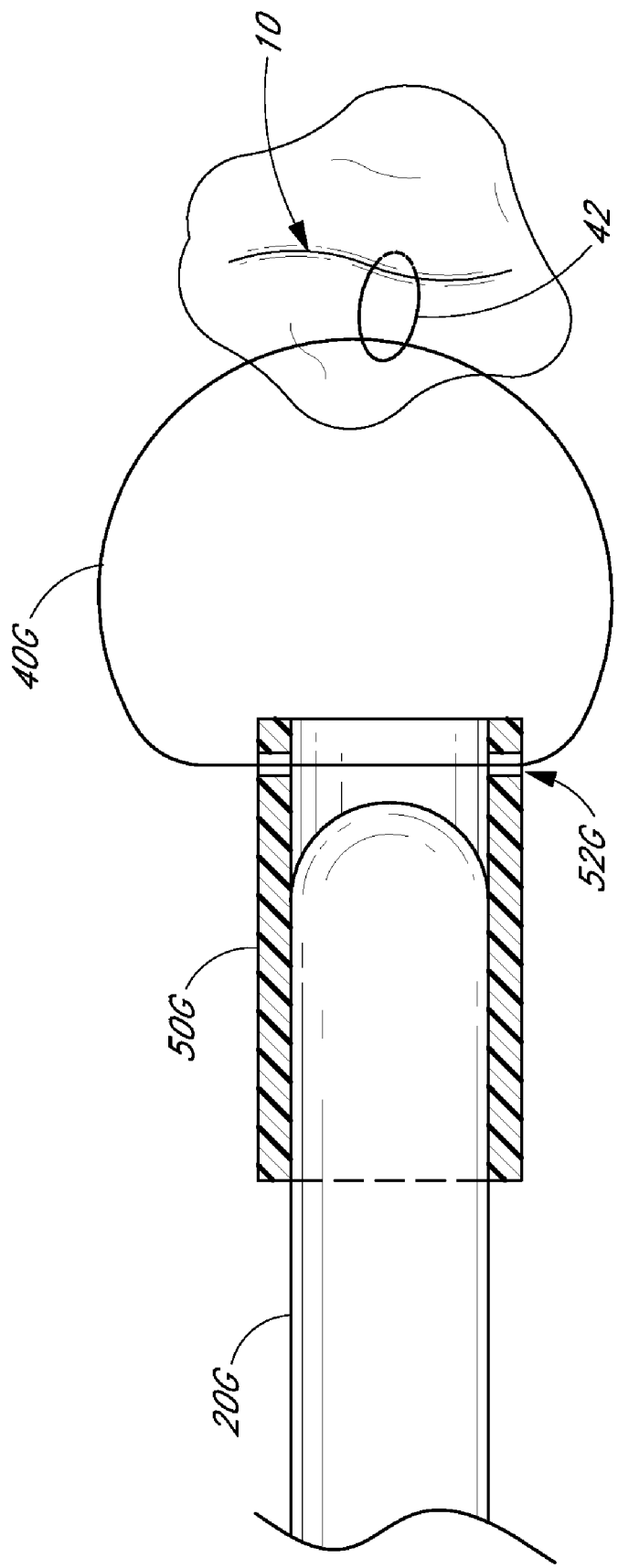
FIG. 9 is a view of a catheter having a tip member secured to its distal end according to another embodiment.

With continued reference to FIG. 9, the anatomy will begin to break down and absorb the biodegradable tip 50G after the passage of a particular time period. Eventually, the tip 50G can detach from the adjoining catheter 20G, allowing the catheter 20G to be withdrawn from the anatomy. The type of biodegradable material, thickness, shape and/or other characteristics of the biodegradable tip 50G can be advantageously selected according to the desired time period for maintaining the catheter 20G within the anatomy. Alternatively, only a portion of the tip 50G may comprise one or more biodegradable materials. For example, the tip 50G may include one or more biodegradable materials only in the areas that adjoin the catheter 20G and/or in the areas surrounding the passage 52G. In some embodiments, biodegradable stitching and/or adhesives may be used to connect the tip 50G to the catheter 20G. Thus, once the stitching and/or adhesive are absorbed by the body, the catheter 20G may be easily removed.

Preferably, in at least some embodiments, the entire tip 50G, the full length of suture filament 40G and all other items used to maintain the catheter 20G near a target anatomical site are manufactured from biodegradable materials so as to eliminate the need for their subsequent removal.

Yet another embodiment of an attachable catheter is illustrated in FIGS. 10 and 11. The depicted catheter 20H includes an enlarged tip 50H at its distal end. As shown, the tip 50H, which has a generally flat, circular shape, includes a passage 52 through which suture filament 40H may be routed. As in other embodiments described herein, the suture filament 40H can be configured to preferably attach to anatomical tissue in order to maintain the catheter 20H in a desired location within the anatomy. The tip 50H and catheter 20H may be manufactured as either a unitary or separate members. In a preferred embodiment, the tip 50H is manufactured from or otherwise comprises one or more biodegradable materials. Thus, after the passage of a particular time period, the tip 50H detaches from the catheter 20H (e.g., along line 54 as shown in FIGS. 10 and 11), allowing the catheter 20H to be withdrawn from the anatomy.

In operation, after the catheter is delivered within a desired location of the anatomy, a suture filament is used to restrict the position of the catheter to a target area. In some embodiments, as illustrated in FIGS. 1, 2A, 3 and 4, a suture filament is routed from the proximal end of the catheter through a transverse opening near the distal portion of the catheter. The suture filament is then secured to anatomical tissue to maintain the position of the catheter. In other embodiments, such as illustrated in FIG. 5, the suture filament is routed through a lumen within the catheter before being attached to anatomical tissue. In yet another arrangement, such as depicted in FIG. 7, the suture filament is directed through a passage located on a tip to which the catheter is attached. In still other embodiments, such as shown in FIGS. 9-11, the suture filament that maintains the position of the catheter within the target anatomical location is not routed to the proximal end of the catheter. Instead, the suture filament more directly attaches the distal portion of the catheter and/or tip to anatomical tissue.

After the catheter has been delivered within the anatomy and generally secured in place using suture filament or the like, the desired medical treatment, procedure and/or other activity may be performed. Subsequently, the catheter may be removed by detaching the suture filament from the catheter. For example, as described herein, the suture filament may be cut, untied, compromised and/or otherwise undone. In other embodiments, the suture filament, catheter tip and/or other members securing the catheter within the anatomy are manufactured from one or more biodegradable materials. Thus, as discussed in greater detail herein, with the passage of time, the biodegradable components will decompose, disintegrate, fragment, dissolve or otherwise become absorbed within the body, allowing the catheter to be easily removed. After the catheter has been removed, it may be necessary to remove one or more non-biodegradable items remaining in the anatomy (e.g., suture filaments, tips, etc.).

The use of a single catheter body with a passage or opening through which a suture filament may be passed provides a simple way of securing a catheter within an anatomical region. In addition, the release features of the devices and methods described herein permit a catheter to by easily removed. In fact, with proper instruction, even non-medical professionals could be permitted to withdraw a catheter from an anatomy. Consequently, the likelihood of damaging the catheter and/or causing harm to the anatomy is greatly reduced or eliminated. Further, the use of biodegradable suture filaments, tips and/or other components may reduce or eliminate the need to perform any procedures following the removal of the catheter.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A catheter for placement in an anatomical region, comprising:
    an elongated catheter body defining a longitudinal axis and having a proximal end portion and a distal end portion, said catheter body defining a lumen extending along said longitudinal axis and terminating in said distal end portion; and
    a passage located within said distal end portion of said catheter body distally beyond said lumen, said passage being integrally formed within said catheter body and extending across said catheter body such that said passage has a directional component generally perpendicular to said longitudinal axis;
    wherein said passage is isolated from said lumen and is configured to accept a filament for securing said catheter to a portion of the anatomical region.

2. The catheter of claim 1, wherein said passage intersects said longitudinal axis.

3. The catheter of claim 1, wherein said distal end portion of said catheter body is substantially flat and said passage is located within said distal end portion.

4. The catheter of claim 3, wherein said distal end portion is substantially circular in shape.

5. A catheter for placement in an anatomical region, comprising:
    an elongated catheter body defining a longitudinal axis and having a proximal end portion and a distal end portion, said catheter body defining a first lumen extending along said longitudinal axis and configured to deliver a fluid between said proximal and distal end portions; and
    a second lumen extending in the direction of the longitudinal axis and isolated from said first lumen and situated within a portion of said catheter body, said second lumen integrally formed within said catheter body and defining a distal opening located in said distal end portion of said catheter body distally beyond the first lumen, and a proximal opening spaced proximally along said longitudinal axis from said distal opening;
    wherein said second lumen is configured to accept a filament for securing said catheter to a portion of said anatomical region, and wherein said portion of said catheter body containing said second lumen has a substantially circular cross-sectional shape.

6. The catheter of claim 5, wherein said second lumen is substantially parallel to said first lumen.

7. The catheter of claim 5, wherein said second lumen extends through only a portion of said catheter body such that said proximal opening exits said catheter body at a location distal to said proximal end of said catheter body.

8. The catheter of claim 5, wherein said catheter body further comprises a slit, said slit configured to permit a filament within said second lumen to pass from said second lumen to outside of said catheter body through said slit.

* * * * *